United States Patent [19]

Lyons et al.

[11] 4,260,808

[45] Apr. 7, 1981

[54] CATALYTIC PROCESS FOR THE CONVERSION OF TOLUENE TO EQUIMOLAR AMOUNTS OF PHENOL ACETATE AND METHYLENE DIACETATE

[75] Inventors: James E. Lyons, Wallingford; George Suld, Springfield; Robert W. Shinn, Aston, all of Pa.

[73] Assignee: Suntech, Inc., Philadelphia, Pa.

[21] Appl. No.: 957,273

[22] Filed: Nov. 3, 1978

Related U.S. Application Data

[63] Continuation-in-part of Ser. No. 945,747, Sep. 25, 1978, abandoned.

[51] Int. Cl.³ .............................................. C07C 67/05
[52] U.S. Cl. .................................... 560/131; 560/241; 562/542; 562/607; 568/302; 568/448; 568/484; 568/602; 568/716; 568/763
[58] Field of Search ............... 568/771, 800, 802, 806; 260/604 R, 606, 601; 560/131, 241; 562/607, 542

[56] References Cited

U.S. PATENT DOCUMENTS

| | | | |
|---|---|---|---|
| 1,595,299 | 8/1962 | Hale | 568/802 |
| 2,456,597 | 12/1948 | Schlesman | 568/800 |
| 3,590,081 | 6/1971 | Ishida et al. | 260/606 |
| 3,804,906 | 4/1974 | McAvoyv | 568/802 |
| 4,056,572 | 11/1977 | Bashkirov et al. | 568/800 |
| 4,191,839 | 4/1980 | Lyons | 560/131 |

FOREIGN PATENT DOCUMENTS

| | | | |
|---|---|---|---|
| 1108256 | 4/1968 | United Kingdom | 568/802 |
| 1244080 | 8/1971 | United Kingdom | 568/800 |
| 329167 | 12/1971 | U.S.S.R. | |
| 321518 | 6/1972 | U.S.S.R. | |

OTHER PUBLICATIONS

Grozhan et al., Doklady Akad. Nauk, SSS 204 N 4,872 (1972).
Shuikin et al., Chem. Abstract, V. 56, p. 3390 (1962).

*Primary Examiner*—Werren B. Lone
*Attorney, Agent, or Firm*—J. Edward Hess; Donald R. Johnson; Stanford M. Back

[57] ABSTRACT

Equimolar amounts of phenol and formaldehyde may be prepared from oxygen and toluene. The catalytic oxidation of toluene, when carried out in the presence of acetic anhydride, forms phenyl acetate and methylene diacetate. Pyrolysis of these two intermediates yields phenol and formaldehyde.

Significant improvements in this process are achieved when the first stage of the reaction is carried out in the presence of $MoO_3$.

In a further embodiment of this invention it has been found that Group VIII dithiosemibenzil compounds, particularly nickel dithiosemibenzil, serves as a superior promoter for the toluene oxidation reaction.

In still a further embodiment of this invention it has been found that persulfate promoters such as potassium persulfate, persulfuric acid, or Caro's dry acid are particularly effective promoters for the toluene oxidation reaction.

In a like manner, hydroquinone or resorcinol may be obtained from cresyl acetates.

13 Claims, 1 Drawing Figure

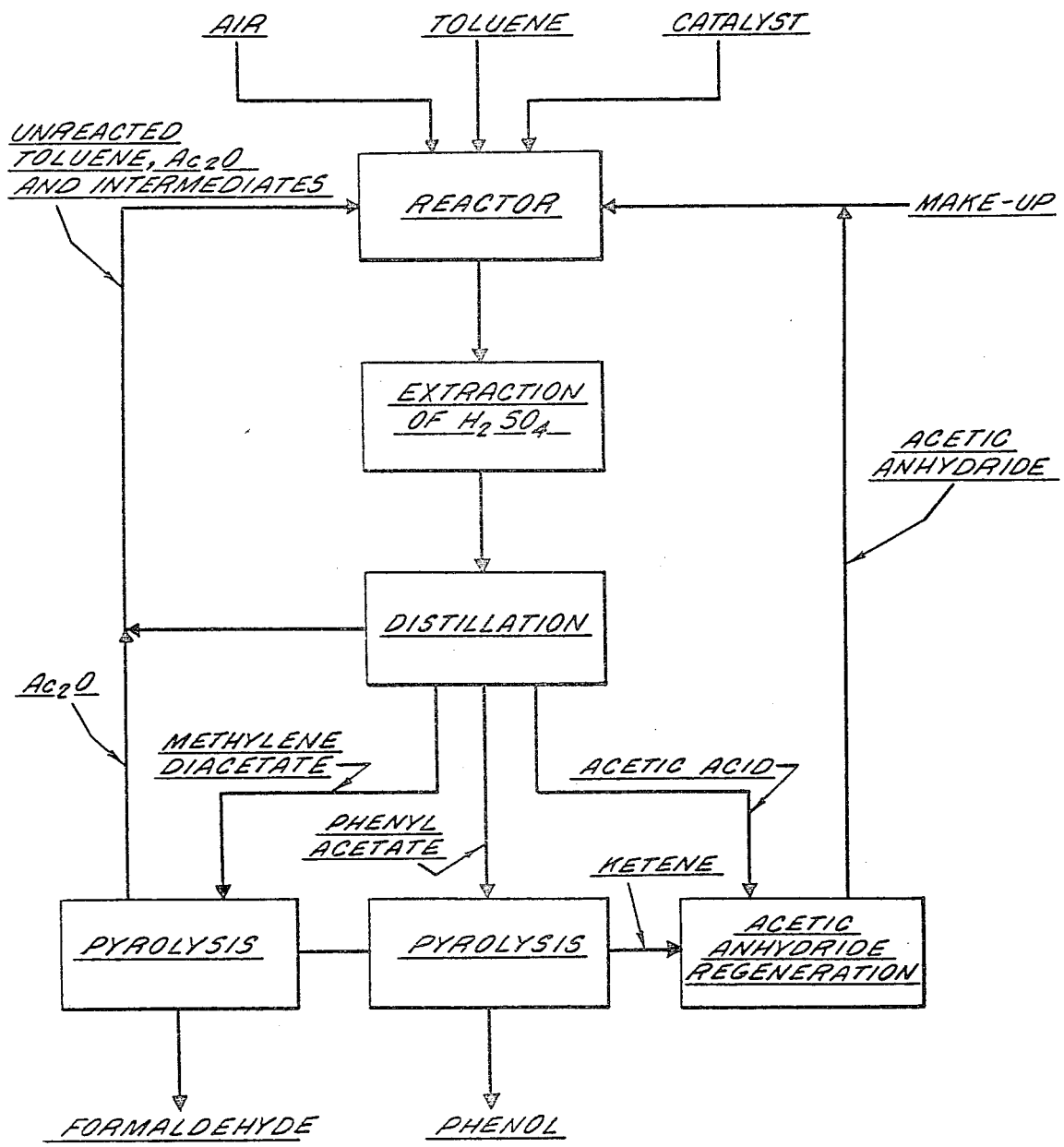

4,260,808

CATALYTIC PROCESS FOR THE CONVERSION OF TOLUENE TO EQUIMOLAR AMOUNTS OF PHENOL ACETATE AND METHYLENE DIACETATE

CROSS-REFERENCE TO RELATED CASES

This application is a continuation-in-part of application Ser. No. 945,747, now abandoned filed Sept. 25, 1978 in the name of Lyons et al.

BACKGROUND OF THE INVENTION

This invention relates to a process for the oxidation of toluene. More particularly, this invention relates to a novel process for the oxidation of toluene to ultimately yield phenol and formaldehyde or paraformaldehyde in equimolar amounts. In a like manner, cresyl acetates may be oxidized to obtain hydroquinone or resorcinol.

It is known from Grozhan et al, Doklady Akad. Nauk SSSR, 204, No. 4,872, and Russian Pat. No. 329,167 (1972) and 321,518 (1971) that when toluene is oxidized in the presence of acetic anhydride and acid, followed by saponification of the total reaction product, phenol is formed in substantial quantities, together with lesser amounts of benzaldehyde, benzyl acetate and other related materials. Counterpart British Pat. No. 1,244,080, from the same Russian sources, teaches a like process and further proposes a mechanism whereby through the formation and rearrangement of a hydroperoxide intermediate, both phenol and an aliphatic aldehyde or ketone are produced.

Significantly, there is no mention or suggestion of the formation of methylene diacetate, and therefore obviously no teaching of converting said methylene diacetate to formaldehyde. Moreover, the Russian work is silent as to the use of any promoters or other adjuvants in addition to acid catalysts which would serve to enhance the rate, yield, or selectivity of this oxidation reaction.

SUMMARY OF THE INVENTION

In accordance with the present invention there is provided a novel process for the oxidation of toluene to ultimately yield equimolar amounts of phenol and formaldehyde or paraformaldehyde. In general, this is achieved by oxidizing toluene with air or oxygen at selected pressures and temperatures in the liquid phase in the presence of acetic anhydride and a strong acid catalyst to form phenyl acetate and methylene diacetate is equal amounts together with acetic acid. The methylene diacetate and phenyl acetate are separated by distillation of the reaction product. The phenyl acetate is then pyrolyzed to form phenol and ketene, while the methylene diacetate is pyrolyzed to form formaldehyde and acetic anhydride. The acetic acid and ketene may then be converted to acetic anhydride by known methods and recycled to the oxidation step.

The oxidation step is further characterized, in accordance with this invention, by the use of molybdenum trioxide for purposes of suppressing the formation of unwanted $CO_2$, or by the use of Group VIII dithiosemibenzil compounds or persulfates as promoters for the oxidation reaction. Optionally, these additives may be employed simultaneously.

Finally, this process is also characterized by the use of certain select temperatures and pressures which further enhance the yield of the desired products.

DESCRIPTION OF THE DRAWING

FIG. 1 is a block flow diagram which shows each aspect of the overall reaction from toluene to final products.

DESCRIPTION OF THE REACTION

As aforementioned, the first step of this process is the liquid phase oxidation of toluene using a strong acid catalyst to form phenyl acetate and methylene diacetate. This reaction may be illustrated as follows:

$$PhCH_3 + O_2 + 2Ac_2O \xrightarrow{H_2SO_4} PhOAc + CH_2(OAc)_2 + HOAc$$

wherein the weight ratio of toluene to acetic anhydride is in the range of from about 50:1 to 1:10, and preferably 10:1 to 2:1, while the ratio of $H_2SO_4$ to toluene employed is from about $5\times10^{-4}$ to $1\times10^{-2}$, and preferably $1\times10^{-3}$ to $5\times10^{31\ 3}$.

The reaction, which employs oxygen or equivalent amounts of air, should be carried out at temperatures in the range of from about 140° to 300° C., and preferably about 150° to 250° C., and at initial pressures of from about 50 to 450 psig. The pressure is desirably generated by charging to an autoclave air or mixtures of oxygen and nitrogen having an oxygen/nitrogen ratio of from 10:1 to 1:20 psig. The reaction mixture is then heated and the reactor pressure rises accordingly.

The reaction may be run in excess toluene as a solvent or in organic solvents such as benzene, chlorobenzene, or acetic acid. Carrying out the reaction in inert solvents such as benzene or chlorobenzene does not appreciably affect yield or selectivity but when acetic acid is employed, significantly increased selectivities may be observed. In order for rapid reactions in acetic acid, promoters such as Caro's dry acid should be employed.

It has been discovered that for purposes of providing a smoothly catalyzed reaction without the formation of considerable quantities of unwanted $CO_2$ by-product, there should desirably be employed in the course of this reaction $MoO_3$. This oxide is preferably added in amounts of $10^{-3}$ to to $10^{-2}$ g per gram of toluene.

In a further embodiment of this invention it has also been found that when a Group VIII dithiosemibenzil complex, such as nickel dithiosemibenzil is added to the reaction it serves as a promoter for the oxidation, thereby increasing the extent of reaction. This promoter is desirably used in amounts of from about $10^{-3}$ to $10^{-2}$ g per gram of toluene.

If desired, both the $MoO_3$ catalyst and the promoters may be used jointly, although this in not essential. However, enhanced results are generally obtained thereby.

The reaction product containing phenyl acetate and methylene diacetate, as well as lesser amounts of such products as benzyl acetate and benzylidene diacetate is then routinely treated to remove the acid catalyst therefrom. The phenyl acetate and methylene diacetate are than separated by distillation under vacuum.

The recovered phenyl acetate is then converted to phenol and ketene by pyrolysis. This is conventionally achieved by heating the phenyl acetate at temperatures of from about 500° to 1000° C., preferably at about 625° C., preferably in the presence of a catalyst such as triethylphosphate, and separating the effluent phenol and ketene by conventional means.

In a like manner, the pyrolysis of methylene diacetate yields formaldehyde and acetic anhydride. This pyrosis is conventionally carried out in one step in a homogeneous gas phase reaction, at about 450°–550° C. under reduced pressure. The ketene recovered from the phenyl acetate pyrolysis, together with the acetic acid recovered from the oxidation of the toluene, may then be converted to acetic anhydride for recycling to the initial oxidation step. This is readily achieved by contacting the gaseous ketene with acetic acid at room temperature in the liquid phase.

The following examples are provided solely for purposes of illustrating but not limiting the novel process of this invention.

EXAMPLE 1

The following ingredients were charged to a 300 ml rocking autoclave reactor:

| toluene | 240 | m mole |
|---|---|---|
| acetic anhydride | 120 | m mole |
| $H_2SO_4$ | 1 | m mole |
| $N_2$ | 230 | psi |
| $O_2$ | 60 | psi |

The temperature was rapidly raised to 203° C. where it was maintained for one hour. At the end of this time rapid cooling was accomplished first by air, then by cold water immerrsion. This was followed by analysis of both the gas and liquid phases. Mass spectrometric analysis of the gas phase together with measurement of pressure decrease showed that the ratio of moles of $CO_2$ produced to moles of $O_2$ consumed was 0.21.

Standardized gas chromatographic analysis of the liquid phase showed that toluene conversion was 9%, and >60% of the acetic anhydride had been consumed.

Product selectivities (%) based on toluene converted were:

| Phenyl acetate | 52 | Methylene diacetate | 52 |
|---|---|---|---|
| o-methyl phenyl acetate | 4 | | |
| benzyl acetate | 16 | | |
| phenoxymethylene acetate | 6 | | |
| benzylidene diacetate | 6 | | |
| tars and others | 16 | | |
| | 100 | | |

EXAMPLE 2

The following ingredients were charged to a 300 ml rocking autoclave reactor:

| toluene | 240 | m mole |
|---|---|---|
| acetic anhydride | 120 | m mole |
| $H_2SO_4$ | 1 | m mole |
| $MoO_3$ | 0.1 | g |
| $N_2$ | 230 | psi |
| $O_2$ | 60 | psi |

The temperature was rapidly raised to 201° C. where it was maintained for one hour. At the end of this time, the product was worked up in accordance with the procedures of Example 1. The ratio of moles of $CO_2$ produced to moles of $O_2$ consumed was 0.08.

Standardized gas chromatographic analysis of the liquid phase showed that toluene conversion was 10%.

Product selectivities (%) based on toluene converted were:

| phenyl acetate | 54 | methylene diacetate | 54 |
|---|---|---|---|
| o-methyl phenyl acetate | 4 | | |
| benzyl acetate | 15 | | |
| phenoxymethylene acetate | 6 | | |
| benzylidene diacetate | 6 | | |
| tars and others | 15 | | |
| | 100 | | |

EXAMPLE 3

The following ingredients were charged to a 300 ml rocking autoclave reactor:

| toluene | 240 | m mole |
|---|---|---|
| acetic anhydride | 120 | m mole |
| $H_2SO_4$ | 1 | m mole |
| $MoO_3$ | 0.1 | g |
| Ni dithiosemibenzil | 0.15 | m mole |
| $N_2$ | 230 | psi |
| $O_2$ | 60 | psi |

The temperature was rapidly raised to 203° C. where it was maintained for one hour. At the end of this time, the product was worked up in accordance with the procedures of Example 1. The ratio of moles of $CO_2$ produced to the moles of $O_2$ consumed was 0.10.

Standardized gas chromatographic analysis of the liquid phase showed that toluene conversion was 16%.

Product selectivities (%) based on toluene converted were:

| phenyl acetate | 50 | methylene diacetate | 51 |
|---|---|---|---|
| o-methyl phenyl acetate | 4 | | |
| benzyl acetate | 18 | | |
| phenoxymethylene acetate | 8 | | |
| benzylidene diacetate | 6 | | |
| tars and others | 14 | | |
| | 100 | | |

A comparison of the $CO_2/O_2$ ratio of Example 1 with that of Examples 2 and 3 clearly demonstrates the effectiveness of $MoO_3$ in suppressing $CO_2$ formation.

EXAMPLE 4

The following ingredients were charged to a 300 ml rocking autoclave reactor:

| toluene | 240 | m mole |
|---|---|---|
| acetic anhydride | 120 | m mole |
| $H_2SO_4$ | 1 | m mole |
| $CrO_3$ | 0.1 | g |
| $N_2$ | 230 | psi |
| $O_2$ | 60 | psi |

The temperature was rapidly raised to 202° C. where it was maintained for one hour. At the end of this time, the product was worked up in accordance with the procedures of Example 1. The ratio of moles of $CO_2$ produced to the moles of $O_2$ consumed was >0.3.

Standardized gas chromatographic analysis of the liquid phase showed that toluene conversion was 11%.

Product selectivities (%) based on toluene converted were:

| phenyl acetate | 20 | methylene diacetate | 19 |
|---|---|---|---|
| o-methyl phenyl acetate | 5 | | |

-continued

| | |
|---|---|
| benzyl acetate | 36 |
| phenoxymethylene acetate | 12 |
| benzylidene diacetate | 16 |
| tars and others | 11 |
| | 100 |

EXAMPLE 5

The following ingredients were charged to a 300 ml rocking autoclave reactor:

| | | |
|---|---|---|
| toluene | 240 | m mole |
| acetic anhydride | 120 | m mole |
| H$_2$SO$_4$ | 1 | m mole |
| WO$_3$ | 0.1 | g |
| N$_2$ | 230 | psi |
| O$_2$ | 60 | psi |

The temperature was rapidly raised to 203° C. where it was maintained for one hour. As the end of this time the product was worked up in accordance with the procedures of Example 1. The ratio of moles of CO$_2$ produced to the moles of O$_2$ consumed was 0.25.

Standardized gas chromatographic analysis of the liquid phase showed that toluene conversion was 8%.

Product selectivities (%) based on toluene converted were:

| | | | |
|---|---|---|---|
| phenyl acetate | 35 | methylene diacetate | 50 |
| o-methyl phenyl acetate | 2 | | |
| benzyl acetate | 35 | | |
| phenoxymethylene acetate | 3 | | |
| benxyldene diacetate | 4 | | |
| tars and others | 21 | | |
| | 100 | | |

A comparsion of the selectivities of Examples 2 and 3, where MoO$_3$ was employed, with the results obtained from CrO$_3$ and WO$_3$ in Examples 4 and 5, will reveal that MoO$_3$ is far superior to these other metals for purposes of obtaining the desired phenyl acetate and methylene diacetate. In addition the MoO$_3$ provided a smoothly catalyzed reaction with little burn to CO$_2$ whereas in the cases of CrO$_3$ and WO$_3$, 2.5 to 4.0 times as much CO$_2$ was produced.

EXAMPLE 6

The following ingredients were charged to a 300 ml rocking autoclave reactor:

| | | |
|---|---|---|
| toluene | 240 | m mole |
| acetic anhydride | 120 | m mole |
| H$_2$SO$_4$ | 1 | m mole |
| K$_2$S$_2$O$_8$ | 0.1 | g |
| N$_2$ | 230 | psi |
| O$_2$ | 60 | psi |

The temperature was rapidly raised to 201° C. where it was maintained for one hour. At the end of this time, the product was worked up in accordance with the procedures of Example 1.

Standardized gas chromatographic analysis of the liquid phase showed that toluene conversion was 16%.

Product selectivities (%) based on toluene converted were:

| | | | |
|---|---|---|---|
| phenyl acetate | 54 | methylene diacetate | 51 |
| o-methyl phenyl acetate | 4 | | |
| benzyl acetate | 15 | | |
| phenoxymethylene acetate | 6 | | |
| benzylidene diacetate | 6 | | |
| tars and others | 15 | | |
| | 100 | | |

EXAMPLE 7

The following ingredients were charged to a 300 ml rocking autoclave reactor:

| | | |
|---|---|---|
| toluene | 240 | m mole |
| acetic anhydride | 120 | m mole |
| H$_2$SO$_4$ | 1 | m mole |
| Dry Caro's acid | 0.5 | g |
| N$_2$ | 230 | psi |
| O$_2$ | 60 | psi |

The temperature was rapidly raised to 203° C. where it was maintained for one hour. At the end of this time, the product was worked up in accordance with the procedures of Example 1.

Standardized gas chromatographic analysis of the liquid phase showed that toluene conversion was 18%.

Product selectivities (%) based on toluene converted were:

| | | | |
|---|---|---|---|
| phenyl acetate | 55 | methylene diacetate | 54 |
| o-methyl phenyl acetate | 4 | | |
| benzyl acetate | 13 | | |
| phenoxymethylene acetate | 6 | | |
| benzylidene diacetate | 6 | | |
| tars and others | 16 | | |
| | 100 | | |

EXAMPLE 8

The following ingredients were charged to a 300 ml rocking autoclave reactor:

| | | |
|---|---|---|
| toluene | 160 | m mole |
| acetic acid | 80 | m mole |
| acetic anhydride | 120 | m mole |
| Dry Caro's Acid | 0.5 | g |
| N$_2$ | 230 | psi |
| O$_2$ | 60 | psi |

The temperature was rapidly raised to 203° C. where it was maintained for 1.5 hours. At the end of this time the product was worked up in accordance with the procedures of Example 1. Toluene conversion was 8%. Product selectivities % based on toluene were:

| | |
|---|---|
| phenyl acetate | 56% |
| methylene diacetate | 58% |
| benzyl acetate | 9% |
| others | 35% |

EXAMPLE 9

Pyrolysis of methylene diacetate to paraformaldehyde and acetic anhydride is accomplished thermally at about 500° C. in a known manner.

Alternatively, the catalytic pyrolysis of methylene diacetate is carried out at about 300° C. in the presence of a catalyst composed of 5% sodium chloride mixed with silica gel dried and calcined. The methylene diacetate, dissolved in n-hexane, is passed through a passified tubular reactor packed with the catalyst at a space velocity of 900 $hr^{-1}$ and a temperature of 300° C. Paraformaldehyde and acetic anhydride condense downstream and are separated routinely. Selectivities exceed 93% for acetic anhydride and 95% for methylene diacetate.

EXAMPLE 10

Pyrolysis of phenyl acetate to phenol and ketene is accomplished thermally at 625° C. by passing it through a wellconditioned tubular reactor. The effluent is condensed to give 84% yield of phenol and 89% yield of ketene.

The reaction may be carried out at a somewhat lower temperature in the presence of triethyl phosphate catalyst at space velocities of between 900 and 1000 $hr^{-1}$. Yields in excess of 90% are obtained.

EXAMPLE 11

Gaseous ketene obtained from phenyl acetate pyrolysis reacts exothermically with acetic acid (distilled from the oxidation reaction product) in a scrubber reactor with sufficient heat removal capacity. Heat of reaction is 15 kcal/mole. The reaction is carried out in two stages at 30°–40° C. and pressures of 50–150 mm Hg. Conversions of acetic acid and ketene to acetic anhydride are 90% and 98% respectively. Selectivity to acetic anhydride exceeds 95%.

In a further embodiment of this invention it has been found that in a manner similar to the above-described process, hydroquinone or resorcinol, and formaldehyde can be co-produced in several steps from p-xylene or m-xylene respectively. For example, p-xylene can be oxidized to p-cresyl acetate in a known manner which can be oxidized further to hydroquinone diacetate in accordance with the process of this invention. The oxidation of each methyl group liberates one molecule of methylene diacetate. Hydroquinone diacetate can be saponified to give hydroquinone and acetic acid.

In this context, it has been found that persulfate promoters enhance the rate and selectivity of oxidation of more complex methyl aromatics such as p-cresyl acetate far more dramatically than they enhance toluene oxidation. For example, it has been found that p-cresyl acetate is oxidized very poorly at 200° C. in the presence of strong acid and acetic anhydride in the absence of persulfate promoters. Bashkirov (British Pat. No. 1,244,080) found that it was necessary to elevate the reaction temperature to 230° C. to achieve oxidation of p-cresyl acetate in the presence of acetic anhydride and selectivity (20%) was very low. The instant process now achieves selectivities to hydroquinone precursors of greater than 60% at temperatures no higher than 200° C. using persulfate promoters, and in addition will isolate methylene diacetate as a co-product in equimolar amounts. The ability to recover methylene diacetate in equimolar amounts in all of these cases is of considerable practical value since one does not lose or waste the methyl group (as$CO_2$) but converts it to a valuable chemical product while at the same time producing the desired phenolic precursor.

The aforementioned persulfate promoter, in one form, can be obtained by admixing potassium persulfate with sodium bisulfate.

EXAMPLE 12

Para-cresyl acetate, 25 ml, benzene, 25 ml, sulfuric acid, 0.12 gram, sodium bisulfate, 0.20 gram, potassium persulfate, 0.20 gram and acetic anhydride, 6.0 ml, were charged to a rocking autoclave and then 290 pounds of a 20/80 oxygen/nitrogen mixture was admitted. The bomb was rocked for 90 minutes at 200° C., cooled, opened and the products analyzed by glpc. Para-cresyl acetate was converted (10%) to methylene diacetate (40% selectivity) hydroquinone diacetate (63% selectivity) and other by-products of oxidation. Selectivities were based on p-cresyl acetate converted.

EXAMPLE 13

Para-cresyl acetate, 25 ml, benzene, 25 ml, sulfuric acid, 0.06 gram, sodium bisulfate, 0.10 gram, potassium persulfate, 0.10 gram and acetic anhydride 6.0 ml were charged to a rocking autoclave and then 290 pounds of a 20/80 oxygen/nitrogen mixture was admitted. The bomb was rocked for 90 minutes at 200° C., cooled, opened and the products analyzed by glpc. Para-cresyl acetate was converted (6%) to methylene diacetate (33% selectivity), hydroquinone diacetate (59% selectivity) and other products.

EXAMPLE 14

Meta-cresyl acetate was oxidized in the manner of Example 1 to give methylene diacetate and resorcinol diacetate together with other by-products of oxidation.

The invention claimed is:

1. In the process for the oxidation of toluene with air or oxygen in the liquid phase under elevated pressures and temperatures in the presence of a strong acid catalyst and acetic anhydride to form phenyl acetate, the improvement wherein the reaction is carried out in a closed system whereby no reaction effluent is removed, thereby forming methylene diacetate in approximately equimolar amounts with the said phenyl acetate, together with minor amounts of acetic acid.

2. The process of claim 1 wherein the pressure is in the range of from about 50 to 450 psig.

3. The process of claim 1 wherein the temperature is in the range of from about 140° to 300° C.

4. The process of claim 1 wherein the acid catalyst is $H_2SO_4$.

5. The process of claim 1 wherein the reaction is carried out in the presence of a suitable organic solvent.

6. The process of claim 5 wherein the solvent is benzene or chlorobenzene.

7. The process of claim 5 wherein the solvent is acetic acid in the presence of a promoter.

8. The process of claim 1 wherein the reaction is carried out in the presence of molybdenum trioxide.

9. The process of claim 1 wherein the reaction is carried out in the presence of a Group VIII metal dithiosemibenzil.

10. The process of claim 9 wherein the dithiosemibenzil is nickel dithiosemibenzil.

11. The process of claim 1 wherein the reaction is carried out in the presence of a persulfate selected from the group consisting of sodium persulfate, potassium persulfate, persulfuric acid and Caro's acid.

12. The process of claim 1 wherein the reaction is carried out in the presence of molybdenum trioxide and a Group VIII metal dithiosemibenzil.

13. The process of claim 1 wherein the reaction is carried out in the presence of molybdenum trioxide and a persulfate selected from the group consisting of sodium persulfate, potassium persulfate, persulfuric acid, and Caro's acid.

* * * * *